United States Patent [19]

Hull, Jr.

[11] Patent Number: 5,189,166
[45] Date of Patent: Feb. 23, 1993

[54] PROCESS FOR THE PREPARATION OF 2-ALKYL-5-HYDROXYPYRIMIDINES FROM 1,3-DIAMINO-2-PROPANOL AND AN ALKANECARBOXYLIC ACID

[75] Inventor: John W. Hull, Jr., Midland, Mich.

[73] Assignee: DowElanco, Indianapolis, Ind.

[21] Appl. No.: 916,298

[22] Filed: Jul. 17, 1992

[51] Int. Cl.$^5$ ............................................. C07D 239/36
[52] U.S. Cl. ................................................... 544/298
[58] Field of Search ........................................ 544/298

[56] References Cited

U.S. PATENT DOCUMENTS 4,880,929 11/1989 Teunissen et al. ................... 544/242

OTHER PUBLICATIONS

A. J. Fatiadi, Synthesis, 65 (1976) and 133 (1976).

H. M. Fales, J. Amer. Chem. Soc., 77, 5118 (1955).

*Primary Examiner*—John M. Ford
*Attorney, Agent, or Firm*—Craig E. Mixan; Kenneth L. Loertscher

[57] ABSTRACT

A process for the efficient manufacture of 2-alkyl-5-hydroxypyrimidines from relatively inexpensive raw materials is provided.

The vapor phase condensation/cyclization of 1,3-diamino-2-propanol and an alkanecarboxylic acid produces an equilibrium mixture of 2-alkyl-5-hydroxytetrahydropyrimidine and 2-alkyl-5-(aminomethyl)oxazoline. After separation from the oxazoline, the tetrahydropyrimidine can be dehydrogenated under mild neutral conditions with manganese dioxide to produce 2-alkyl-5-hydroxypyrimidines.

10 Claims, No Drawings

PROCESS FOR THE PREPARATION OF 2-ALKYL-5-HYDROXYPYRIMIDINES FROM 1,3-DIAMINO-2-PROPANOL AND AN ALKANECARBOXYLIC ACID

FIELD OF THE INVENTION

The present invention concerns a process for preparing 2-alkyl-5-hydroxypyrimidines directly from 1,3-diamino-2-propanol and an alkanecarboxylic acid. A key part of the process concerns the dehydrogenation of the intermediate 2-alkyl-5-hydroxy-1,4,5,6-tetrahydropyrimidine with manganese dioxide.

BACKGROUND OF THE INVENTION

2-Alkyl-5-hydroxypyrimidines, particularly the 2-t-butyl homolog, are advantageously employed as intermediates for the preparation of insecticidal O-5-pyrimidinyl phosphorothioates as described, for example, in U.S. Pat. Nos. 4,127,652 and 4,729,987. Typically, 2-alkyl-5-hydroxypyrimidines are prepared from the corresponding 2-alkylpyrimidine by selective halogenation of the 5-position followed by hydrolysis to the 5-hydroxy analog.

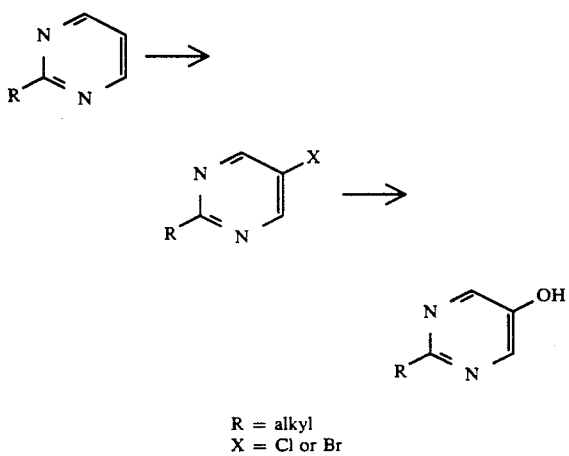

R = alkyl
X = Cl or Br

Although fraught with difficulties, 2-alkyl-5-hydroxypyrimidines can be successfully prepared by this conventional approach; see, for example, U.S. Pat. No. 4,486,590 concerning chlorination and U.S. Pat. No. 4,379,930 concerning hydrolysis. Nevertheless, this scheme is not as straightforward as it appears to be.

Since most 2-alkylpyrimidines are not commercially available, the starting materials for this route must themselves be prepared. This is usually accomplished by reacting an alkanecarboxylic acid (RCO$_2$H) with 1,3-diaminopropane in the vapor phase; see, for example, U.S. Pat. No. 4,999,427. This reaction first involves a condensation/cyclization to an intermediate 2-alkyl-1,4,5,6-tetrahydropyrimidine followed by dehydrogenation to the 2-alkylpyrimidine. Thus, for example, 2-t-butyl-5-hydroxypyrimidine would typically be prepared from pivalic acid and 1,3-diaminopropane by the following scheme.

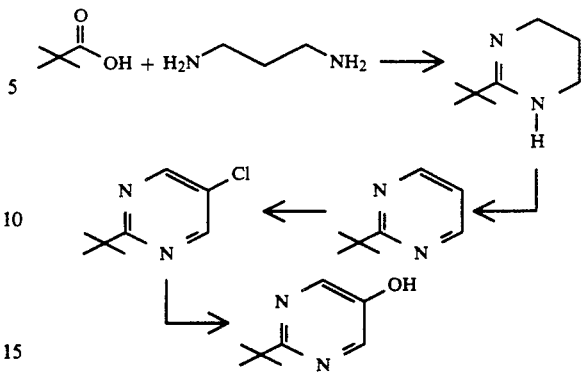

It would be highly desirable to have a more direct route to 2-alkyl-5-hydroxypyrimidines that would entail fewer steps and fewer unit operations.

One approach to abbreviating the conventional scheme would be to employ an acyclic raw material already functionalized with oxygen which, when cyclized, would incorporate the oxygen functionality in the proper ring position. In accord with this approach, U.S. Pat. No. 4,880,929 discloses the cyclization of pivalic acid and 1,3-diamino-2-propanol to 2-t-butyl-5-hydroxy-1,4,5,6-tetrahydropyrimidine. However, this patent remains surprisingly silent concerning the subsequent dehydrogenation of this intermediate to the corresponding pyrimidinol.

SUMMARY OF THE INVENTION

We have now found that the vapor phase reaction of an alkanecarboxylic acid with 1,3-diamino-2-propanol, rather than directly producing a 2-alkyl-5-hydroxy-1,4,5,6-tetrahydropyrimidine, produces as equilibrium mixture of the 2-alkyl-5-hydroxy-1,4,5,6-tetrahydropyrimidine (I) and the isomeric 2-alkyl-5-(aminomethyl)-oxazoline (II); see Scheme A.

Scheme A

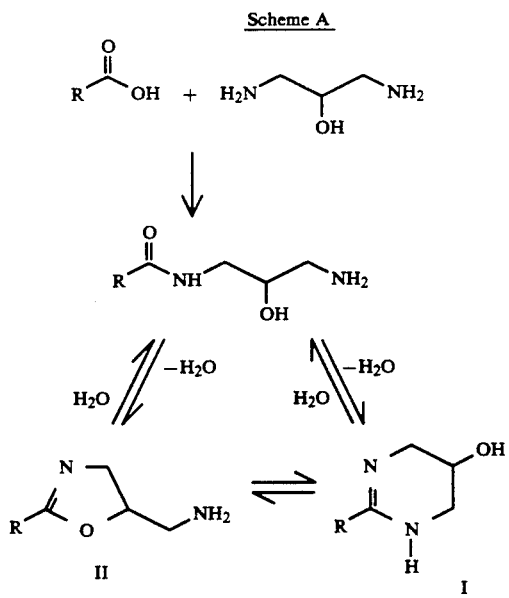

Whether because of the equilibrium between the tetrahydropyrimidine and the oxazoline or because of the presence of the hydroxyl group, the catalytic dehydrogenation of the 2-alkyl-5-hydroxy-1,4,5,6-tetrahydropyrimidine could not be effected in the vapor phase, particularly with the preferred platinum and palladium catalyst of the prior art. The present invention concerns a process for the preparation of 2-alkyl-5-hydroxypyrimidines of the formula

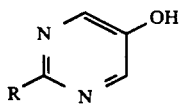

wherein R represents an alkyl group of from 1 to 4 carbon atoms which comprises contacting a 2-alkyl-5-hydroxy-1,4,5,6-tetrahydropyrimidine of the formula

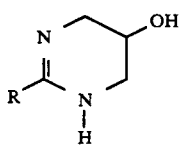

wherein R is as previously defined with at least 2 equivalents of manganese dioxide at a temperature of from about 25° to about 120° C.

Another aspect of the present invention concerns a process for the preparation of 2-alkyl-5-hydroxypyrimidines of formula

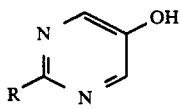

wherein R represents an alkyl group of from 1 to 4 carbon atoms which comprises the following steps:

(a) contacting in the vapor phase from about 0.5 to about 2 molar equivalents of 1,3-diamino-2-propanol with 1 molar equivalent of an alkanecarboxylic acid

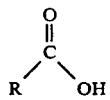

wherein R is as previously defined at a temperature from about 200° to 300° C. over an alumina catalyst to give an equilibrium mixture of 2-alkyl-5-hydroxy-1,4,5,6-tetrahydropyrimidine and 2-alkyl-5-(aminomethyl)oxazoline

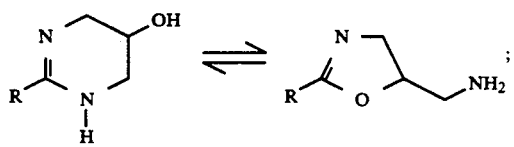

(b) isolating the 2-alkyl-5-hydroxy-1,4,5,6-tetrahydropyrimidine from the 2-alkyl-5-(aminomethyl)oxazoline; and (c) contacting the 2-alkyl-5-hydroxy-1,4,5,6-tetrahydropyrimidine with at least 2 equivalents of manganese dioxide at a temperature of from about 25° to 120° C.

Thus, the desired 2-alkyl-5-hydroxypyrimidines can be prepared from relatively inexpensive starting materials in fewer steps than hitherto possible.

DETAILED DESCRIPTION OF THE INVENTION

The present invention is directed to various aspects of the conversion of alkanecarboxylic acids to 2-alkyl-5-hydroxypyrimidines. As used herein, the terms "alkane" and "alkyl" refer to a straight-chained or branched hydrocarbon group of from 1 to 4 carbon atoms inclusive. Branched alkyl groups of from 3 to 4 carbon atoms are preferred. Iso-propyl and tert-butyl groups are most preferred. All of the 1 to 4 carbon atom alkanecarboxylic acids are commercially available starting materials.

Likewise, 1,3-diamino-2-propanol is a known compound which may be conveniently prepared from epichlorohydrin and ammonia; see U.S. Pat. No. 3,432,553.

Various grades of manganese dioxide are commercially available or can be prepared in the laboratory, e.g., see J. Fatiadi, *Synthesis*, 65 and 133 (1976). Typically, "activated" grades, such as those commercially available, are superior to non-activated $MnO_2$ and can be used directly as supplied by the manufacturer.

The vapor phase condensation/cyclization of 1,3-diamino-2-propanol and an alkanecarboxylic acid has been described in U.S. Pat. No. 4,880,929. In general, the ingredients are contacted in the vapor phase over a Lewis acid catalyst, preferably an alumina catalyst of high surface area and high porosity. Like other vapor phase reactions, the reactants and an appropriate diluent are mixed and passed over the catalyst at a contact time and temperature sufficient to achieve the desired conversion. Typically, an inert gas such as nitrogen is employed as a diluent. The mole ratio of diluent to starting materials can be from about 1:1 to about 50:1. Approximately 2 to 5 moles of diluent per mole of reactants are preferred. The reaction can be conducted with or without an additional solvent. Any solvent capable of dissolving the salt of the alkanecarboxylic acid and the 1,3-diamino-2-propanol is suitable for the process. Water is generally preferred if the use of a solvent is elected. The mole ratio of solvent to starting materials can be from about 0.5:1 to about 50:1. Approximately 1 to 5 moles of solvent per mole of reactants are preferred.

While near stoichiometric ratios of alkanecarboxylic acid to 1,3-diamino-2-propanol are usually preferred, either reactant can be used in excess. Mole ratios of from about 1.1 to about 1.5 of diaminopropanol to alkanecarboxylic acid, however, are most preferred. For convenience, a single feed containing both reactants and a solvent can be employed or the two reactants can be introduced separately into the catalyst bed, thus reducing the amount of solvent required.

Although the exact residence time is not critical, in order to prevent unnecessary degradation, the reactants should not be permitted to remain in contact with the catalyst for a prolonged period. The preferred contact period or residence time, which depends on several factors including temperature, is readily determined by routine experimentation. Temperatures of from about 250° to about 300° C. provide reasonable reaction rates without appreciable by-product formation. Temperatures of about 260° to about 285° C. are preferred.

Operating pressures are not critical and may vary from subatmospheric to somewhat superatmospheric. Operation at atmospheric pressure is most convenient and is preferred.

In a typical reaction, the alkanecarboxylic acid and the 1,3-diamino-2-propanol are mixed in an appropriate solvent such as water and the mixture together with a gaseous diluent is passed over an alumina catalyst bed at a temperature of about 275° C. The effluent from the alumina bed consists predominantly of an equilibrium mixture of the 5-membered ring 2-alkyl-5-(aminomethyl)oxazoline and the 6-membered ring 2-alkyl-5-hydroxy-1,4,5,6-tetrahydropyrimidine.

Where the alkyl group is tert-butyl, the oxazoline is a liquid and the tetrahydropyrimidine is a solid with a tendency to form insoluble crystals. While the oxazoline may be the favored species at higher temperatures, the equilibrium can be shifted in favor of the tetrahydropyrimidine by the formation of insoluble crystals which effectively remove the latter from the equilibrium. Thus, isolated pure oxazoline, an oil at 25° C., very gradually solidifies when standing as it is slowly converted to the tetrahydropyrimidine.

The conversion of 2-t-buty-5-(aminomethyl)oxazoline to 2-t-butyl-5-hydroxy-1,4,5,6-tetrahydropyrimidine can be accelerated by heating. For example, by heating the oxazoline at 80° C. overnight, an equilibrium mixture of oxazoline and tetrahydropyrimidine is formed from which the latter solidifies and can be readily separated. Thus, the effluent from the alumina reaction bed which consists of a mixture of oxazoline and tetrahydropyrimidine is first concentrated under reduced pressure to remove any aqueous solvent. The mixture is then slurried with a solvent which will dissolve the oxazoline but in which the tetrahydropyrimidine is relatively insoluble. Acetonitrile is such an appropriate solvent. The solid tetrahydropyrimidine is isolated by filtration and the oxazoline can be recovered from the filtrate and subsequently equilibrated once again. In this manner, 2-t-butyl-5-hydroxy-1,4,5,6-tetrahydropyrimidine can be recovered in good yield from the effluent mixture exiting the vapor phase reactor.

Conversely, the 2-t-butyl-5-hydroxy-1,4,5,6-tetrahydropyrimidine, when heated above 100° C. such as in refluxing toluene, gradually dissolves as it is converted to the equilibrium mixture of oxazoline and tetrahydropyrimidine. After cooling the solution and after removing the insoluble tetrahydropyrimidine by filtration, relatively pure oxazoline can be recovered by evaporation of the solvent from the filtrate. Thus, for example, either 2-t-butyl-5-hydroxy-1,4,5,6-tetrahydropyrimidine or 2-t-butyl-5-(aminomethyl)oxazoline can be separated from one another.

Because the oxazoline predominates at the high temperatures required for a vapor phase reaction and because the tetrahydropyrimidine is converted back to the oxazoline above about 100° C., the dehydrogenation of the 2-alkyl-5-hydroxy-1,4,5,6-tetrahydropyrimidine needs to be conducted at a temperature lower than that usually encountered in the vapor phase. Solid manganese dioxide has been found to be a mild oxidizing agent in neutral media capable of effecting the dehydrogenation of the 2-alkyl-5-hydroxy-1,4,5,6-tetrahydropyrimidine to the 2-alkyl-5-hydroxypyrimidine. While the dehydrogenation can be run between 25° and 120° C., because lower temperatures provide better yields and less by-products, temperatures of from 25° to 100° C. are preferred. Temperatures of from 25° to 80° C. are most preferred.

The manganese dioxide is typically used in excess. At least 2 molar equivalents of $MnO_2$ are required for each equivalent of tetrahydropyrimidine to be dehydrogenated. From 5 to 15 molar equivalents of $MnO_2$ are preferred.

The dehydrogenation is run in inert organic solvents which do not compete with the substrate for adsorption on the surface of the $MnO_2$. Suitable inert solvents include, for example, saturated hydrocarbons (e.g., hexane, cyclohexane), chlorinated hydrocarbons (e.g., chloroform, methylene chloride), aromatic hydrocarbons (e.g., toluene, chlorobenzene) and tertiary alcohols (e.g., t-butyl alcohol). Although secondary alcohols usually compete with the adsorption of the substrate on the $MnO_2$ surface, iso-propyl alcohol also gives satisfying results. More surprisingly, the reaction can even be run with no solvent by shaking the two solid reactants together at 25° C. Nevertheless, the reaction is preferably conducted in t-butyl alcohol, isopropyl alcohol, toluene or chloroform.

In a typical reaction, the tetrahydropyrimidine and the $MnO_2$ are slurried in a suitable solvent and stirred at a temperature usually below 100° C. The starting 2-alkyl-5-hydroxytetrahydropyrimidine is a strong amidine base ($pK_a \sim 12$) while the product 2-alkyl-5-hydroxypyrimidine is a weak acid ($pK_a \sim 8$). Thus as the reaction proceeds, the product protonates the starting material.

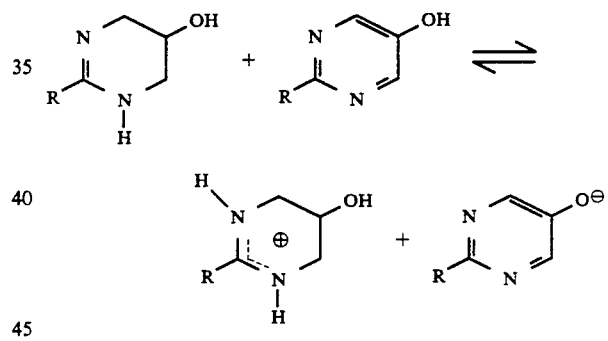

Since the protonated starting material is not readily dehydrogenated, the reaction progresses to 50 percent conversion, at which point all of the starting material is protonated and the reaction slows dramatically. The addition of a base such as caustic or alkoxide, while deprotonating the starting material, itself dramatically retards the reaction rate. Thus it becomes preferable to run the reaction to only 50 percent conversion and to separate the 2-alkyl-5-hydroxypyrimidine from the unreacted 2-alkyl-5-hydroxy-1,4,5,6-tetrahydropyrimidine. The separation can be done, for example, by adding aqueous HCl to an aqueous mixture of the pyrimidine/tetrahydropyrimidine to adjust the pH to about 4. The 2-alkyl-5-hydroxypyrimidine can be obtained by extraction with an immiscible organic solvent, leaving the HCl salt of the 2-alkyl-5-hydroxytetrahydropyrimidine in the aqueous layer from which it can be recovered and recycled.

The following examples are presented to illustrate the invention and should not be construed as limiting the scope of the invention. All melting points are uncorrected unless otherwise noted.

EXAMPLE 1

Preparation of 2-t-Butyl-5-hydroxy-1,4,5,6-tetrahydropyrimidine from Pivalic Acid and 1,3-Diamino-2-propanol The reactor consisted of a 1 inch (") diameter quartz tube heated by an electric 3-zone furnace. The catalyst bed consisted of 73 grams (g) of ⅛" alumina spheres (Alcoa CSS-300 LDS) (15" length by 1" diameter) with the filler regions of the tube occupied by inert quartz chips. A short preheater tube was attached to the top of the reactor.

The feed solution was comprised of 41.4 percent pivalic acid, 43.9 percent 1,3-diamino-2-propanol, and 14.6 percent water, corresponding to a 1/1.2/2 molar ratio, and was kept warm on a hot plate stirrer and pumped through a heated line to the catalyst bed. Pivalic acid (167.4 g, 1.64 mol), 1,3-diamino-2-propanol (177.5 g, 1.97 mol), and water (59.0 g, 3.28 mol) were pumped as a single feed to the alumina bed held at 275° C., at a rate of 1.5 g/min. A preheater tube held at 250° C. served to vaporize the feed components. A nitrogen flow rate of 210 mL/min was applied to the reactor during the run. The reactor effluent was condensed with a hot water condenser to prevent crystallization. The product consisted of an orange oil containing crystalline solid and was stripped on a rotary evaporator to remove water. A roughly equal volume of acetonitrile was added, the slurry cooled to 0° C., and crystalline product was collected on a filter and dried in a vacuum oven at 60° C. to give 139.2 g of 2-t-butyl-5-hydroxy-1,4,5,6-tetrahydropyrimidine as a first crop. The mother liquor was reduced in volume to give an orange oil and placed in an oven at 80° C. overnight. After addition of acetonitrile to the resulting solid and filtration as above, an additional 60.1 g solid was obtained, which was 84 percent pure, most of the remainder being uncyclized materials. The total of 189.7 g of 2-t-butyl-5-hydroxy-1,4,5,6-tetrahydropyrimidine represented a 74 percent isolated yield based on pivalic acid, and a 62 percent yield based on 1,3-diamino-2-propanol. A pure sample was prepared by recrystallization from warm $CH_3CN$: mp 212°-214° C. (corrected, decomp); $^1H$ NMR ($D_2O/CD_3CN$) δ 3.9 (m, 1H), 3.1 (apparent dt, 2H), 2.9 (apparent dd, 2H), 1.0 ppm (s, 3H); $^{13}C$ NMR {$^1H$} ($D_2O/CD_3CN$) δ 168.7 (1 C), 60.0 (1 C), 47.0 (2 C), 37.0 (1 C), 27.7 ppm (3 C); Anal. Calcd for $C_8H_{16}N_2O$: C, 61.50; H, 10.32; N, 17.93. Found: C, 61.57; H, 10.50; N, 18.01.

EXAMPLE 2

Preparation of 2-t-Butyl-5-(aminomethyl)oxazoline

Solid 2-t-butyl-5-hydroxy-1,4,5,6-tetrahydropyrimidine (2.55 g, 1.63 mmol) was heated to reflux in 100 mL of toluene for 22 hours. The solution was cooled to 25° C. and the slurry was filtered to remove 0.91 g of unconverted tetrahydropyrimidine after drying. The toluene filtrate was evaporated to give 1.17 g of 2-t-butyl-5-(aminomethyl)oxazoline as an oil: $^1H$ NMR ($CDCl_3$) δ 4.5 (m, 1H), 3.8 (apparent dd, 1H), 3.5 (apparent dd, 1H), 2.8 (apparent dq, 2H), 1.2 ppm (s, 9H), $^{13}C$ NMR {$^1H$} ($CDCl_3$) δ 173.3 (1 C), 80.1 (1 C), 56.4 (1 C), 45.3 (1 C), 32.5 (1 C), 27.1 ppm (3 C). The neat oil gradually solidifies over a number of days, even at 0° C., reverting back to the tetrahydropyrimidine.

EXAMPLE 3

Preparation of 2-t-Butyl-5-hydroxypyrimidine

Solid 2-t-butyl-5-hydroxy-1,4,5,6-tetrahydropyrimidine (40.25 g, 0.26 mol) and activated $MnO_2$ (201.75 g, 2.32 mol) were placed into a 2-liter 3-necked round-bottom flask fitted with an overhead stirrer. The reactor was purged with argon and 600 mL of t-butanol were added. The slurry was stirred at 25° C. for 15 days, then diluted with about 200 mL of $CH_3OH$ and filtered through celite on a glass filter, rinsing the filter cake with excess $CH_3OH$. The filtrate was evaporated to give 46.9 g of solid residue, which is a mixture of starting material and desired product. The mixture was dissolved in 200 mL of $H_2O$ and the pH reduced to 5.0 with 37 percent HCl, resulting in the precipitation of 2-t-butyl-5-hydroxypyrimidine as an oil. This mixture was extracted with $CH_2Cl_2$, and the organic phase evaporated to give 16.41 g of product as a tan crystalline solid, mp 126°-129° C., for a yield of 41 percent: $^{13}C$ NMR {$^1H$} ($CDCl_3$) δ 168.5 (1 C), 149.7 (1 C), 144.2 (2 C), 38.8 (1 C), 29.7 ppm (3 C).

Table I summarizes additional dehydrogenations performed according to procedures similar to Example 3.

TABLE I

Manganese Dioxide Dehydrogenations of 2-t-Butyl-5-hydroxy-1,4,5,6-tetrahydropyrimidine

|  |  |  |  |
|---|---|---|---|
| A | $\xrightarrow[\sim 50\% \text{ conv.}]{MnO_2}$ | B |
| MW 156.23 | 86.94 | 152.20 |

| A mmole | $MnO_2$ mmole | Temp °C. | Solvent | Time hrs | B mmole | % yield* |
|---|---|---|---|---|---|---|
| 30 | 410 | 60° C. | $C_6H_5CH_3$ | 40 | 8.1 | 27% |
| 12 | 111 | 83° C. | t-BuOH | 6 | 4 | 33% |
| 19 | 173 | 83° C. | t-BuOH | 14.5 | 9.5 | 50% |
| 13 | 116 | 25° C. | t-BuOH | 355 | 5.3 | 41% |
| 129 | 1150 | 25° C. | i-PrOH | 187 | 39 | 30% |
| 80 | 725 | 61° C. | $CHCl_3$ | 7 | 11 | 14% |
| 129 | 1150 | 25° C. | hexane | 69 | 15 | 12% |

*yield of B based on amount of A charged irrespective of conversion

What is claimed is:

1. A process for the preparation of 2-alkyl-5-hydroxypyrimidines of the formula

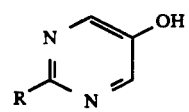

wherein R represents an alkyl group of from 1 to 4 carbon atoms which comprises contacting a 2-alkyl-5-hydroxy-1,4,5,6-tetrahydropyrimidine of the formula

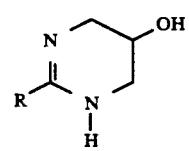

wherein R is as previously defined with at least 2 equivalents of manganese dioxide at a temperature of from about 25° to about 120° C.

2. The process of claim 1 in which from 5 to 15 molar equivalents of manganese dioxide are employed per equivalent of 2-alkyl-5-hydroxy-1,4,5,6-tetrahydropyrimidine.

3. The process of claim 1 in which R is t-butyl.

4. The process of claim 1 in which the temperature is from about 25° to about 100° C.

5. The process of claim 4 in which the temperature is from about 25° to about 80° C.

6. The process of claim 1 in which the reaction is conducted in an inert solvent selected from the group consisting of saturated hydrocarbons, chlorinated hydrocarbons, aromatic hydrocarbons and tertiary alcohols.

7. A process for the preparation of 2-alkyl-5-hydroxypyrimidines of formula

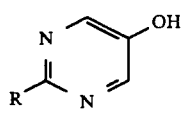

wherein R represents an alkyl group of from 1 to 4 carbon atoms which comprises the following steps:
(a) contacting in the vapor phase from about 0.5 to about 2 molar equivalents of 1,3-diamino-2-propanol with 1 molar equivalent of an alkanecarboxylic acid $$\underset{R}{\overset{O}{\underset{\|}{C}}}\diagdown OH$$

wherein R is as previously defined at a temperature from about 200° to 300° over an alumina catalyst to give an equilibrium mixture of 2-alkyl-5-hydroxy-1,4,5,6-tetrahydropyrimidine and 2-alkyl-5-(aminomethyl) oxazoline

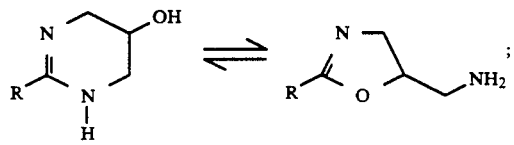

(b) isolating the 2-alkyl-5-hydroxy-1,4,5,6-tetrahydropyrimidine from the 2-alkyl-5-(aminomethyl)oxazoline; and
(c) contacting the 2-alkyl-5-hydroxy-1,4,5,6-tetrahydropyrimidine with at least 2 equivalents of manganese dioxide at a temperature of from about 25° to about 120° C.

8. The process of claim 7 in which from 5 to 15 equivalents of manganese dioxide are employed per equivalent of 2-alkyl-5-hydroxy-1,4,5,6-tetrahydropyrimidine.

9. The process of claim 7 in which R is t-butyl.

10. The process of claim 7 in which the dehydrogenation (step (C)) is run at a temperature from about 25° to about 80° C.

* * * * *